United States Patent
Marcon et al.

(10) Patent No.: US 6,619,299 B2
(45) Date of Patent: Sep. 16, 2003

(54) FLAVOR ENHANCED WHITENING DENTAL FLOSS

(76) Inventors: Robert Victor Marcon, 3471 Sinnicks Avenue, Niagara Falls Ont. (CA), L2J 2G6; Lawrence Wayne Nash, 17 Beachview Drive, St. Catharines Ont. (CA), L2N 3W2

(*) Notice: Subject to any disclaimer, the term of this patent is extended or adjusted under 35 U.S.C. 154(b) by 0 days.

(21) Appl. No.: 10/023,355

(22) Filed: Dec. 17, 2001

(65) Prior Publication Data

US 2002/0112737 A1 Aug. 22, 2002

Related U.S. Application Data

(60) Provisional application No. 60/255,822, filed on Dec. 18, 2000.

(51) Int. Cl.⁷ ............................................. A61C 15/00
(52) U.S. Cl. ...................... 132/321; 132/200; 424/49
(58) Field of Search ............................. 132/321, 323, 132/324, 325, 326, 327, 328, 329, 200; 424/52, 58, 48, 53, 49

(56) References Cited

U.S. PATENT DOCUMENTS

| | | | | | |
|---|---|---|---|---|---|
| 3,838,702 A | * | 10/1974 | Standish et al. | ............. | 132/321 |
| 3,897,795 A | * | 8/1975 | Engel | ........................ | 132/321 |
| 3,943,949 A | * | 3/1976 | Ashton et al. | ............... | 132/321 |
| 4,335,102 A | * | 6/1982 | Nakashima et al. | ........... | 424/52 |
| 4,983,404 A | * | 1/1991 | Raman et al. | .................. | 426/3 |
| 5,357,990 A | * | 10/1994 | Suhonen et al. | ............. | 132/321 |
| 5,607,681 A | * | 3/1997 | Galley et al. | ................ | 424/405 |
| 5,880,076 A | * | 3/1999 | Vermeer | ....................... | 510/123 |
| 5,967,153 A | * | 10/1999 | Mitha et al. | ................. | 132/321 |
| 5,967,155 A | * | 10/1999 | Marcon | ...................... | 132/321 |
| 6,080,481 A | * | 6/2000 | Ochs et al. | .................. | 428/372 |
| 6,102,050 A | * | 8/2000 | Marcon | ...................... | 132/321 |
| 6,145,516 A | * | 11/2000 | Guay et al. | .................. | 132/321 |

* cited by examiner

*Primary Examiner*—Kevin Shaver
*Assistant Examiner*—David C Comstock

(57) ABSTRACT

The present invention relates to a flavor enhanced whitening dental floss that comprises a dental floss and various whitening formulations that taste remarkably good. Regular use of such a floss will therefore provide not only a significant improvement in the interproximal and subgingival whiteness of teeth but also provide all other benefits normally associated with flossing. As a result, consumers will now be able to achieve better overall results; inexpensively, safely, and in a much more pleasurable manner than is otherwise possible.

21 Claims, No Drawings

FLAVOR ENHANCED WHITENING DENTAL FLOSS

CROSS-REFERENCE

This application claims priority from U.S.A. Provisional Application, Ser. No. 60/255,822, filed Dec. 18, 2000.

FEDERALLY SPONSORED RESEARCH OR DEVELOPMENT STATEMENTS

Not applicable.

REFERENCE TO A MICROFICHE APPENDIX

Not applicable.

BACKGROUND OF THE INVENTION

This invention relates to dental flosses and, specifically, to flavour enhanced whitening dental flosses (FEWD flosses) which reduce dental decay, whiten teeth, and taste remarkably good.

It is generally recognized by the dental profession that plaques, including those that are found between the interproximal surfaces of teeth, are a major cause of both dental decay and inflammatory periodontal disease. These plaques, which can contain 250 or more separate microbial species, use sugars and other fermentable carbohydrates to produce polymers which bind the organisms to the surface of teeth and acids which cause their demineralization. In the first stages, a carious lesion does not contain an actual cavity but with prolonged and repeated demineralization by these plaque created acids, a cavity will form. Thus, each time something sweet is consumed plaques produce approximately 20 minutes of oral acid which, in turn, seriously contributes to dental demineralization.

Furthermore, plaques, if not removed will in time form calculus, and calculus, is the mineralized bacterial plaque deposits found on teeth, restorations, and other solid oral structures. Invariably, calculus is covered by a film of plaque, the organisms of which also occupy its porous structure. Its composition is generally made up of seventy percent organic salts, and a thirty percent combination of micro-organisms and organic material. Moreover, its formation is always preceded by plaque accumulation which serves as an organic matrix for the subsequent mineralization of the deposit. Mineralization, by the precipitation of the mineral salts in plaque can start at any time from the second to the fourteenth day of plaque formation, but some individuals can begin to calcify plaque in four to eight hours. Initially, small crystals develop close to these bacteria. Then, gradually, the intermicrobial matrix becomes entirely calcified and eventually the bacteria itself also becomes mineralized.

As a result, the presence of calculus not only makes effective oral hygiene impossible but can also seriously irritate gum tissues. Thus, its prevention and or removal to help control the inception or progression of inflammatory periodontal disease is of great importance. It is also the reason why dental professionals have always recommended flossing, in addition to the conventional practice of using a brush and dentifrice, for flossing clears the interproximal surfaces of the teeth in a manner that a toothbrush, with or without a dentifrice, cannot achieve. With this two step cleaning method effective oral hygiene is, therefore, greatly improved.

In addition to the various problems created by plaques consumers have always desired the cosmetic beauty of white shiny teeth. However, the stains and discolorment found in and around the interproximal surfaces of teeth are not only difficult to remove but are also difficult to prevent. Moreover, treatments for this condition are only available from professional dental practitioners, certain dentifrices, some mouthwashes, and one floss. Unfortunately, professional dental practitioners are invariably expensive, time consuming, and not always effective, whereas, a brush and dentifrice alone are ineffective in cleaning, let alone actually whitening, the interproximal surfaces of teeth. Mouthwashes have been suggested by the prior art but as yet no commercial products have been realized that can efficiently clean or whiten these interproximal dental surfaces. A whitening floss has also been suggested by the prior art—specifically U.S. Pat. No. 6,102,050. However, this floss, while effective, releases only modest levels of flavouring.

As a result, there is presently an unfulfilled need in the general public for a convenient, effective, and inexpensive solution to help whiten interproximal and subgingival dental surfaces, maintain this whiteness over extended periods, and to do it in a good tasting and pleasant manner. To this end, the invention detailed herein addresses these failings by providing a more effective and desirable solution than can be currently achieved.

OBJECTS AND ADVANTAGES

The invention disclosed herein overcomes many of the drawbacks listed in the prior art while also providing a more effective solution and improved performance over presently used dental flosses. In addition, some of the objects and advantages associated with this invention are described below. Others will become apparent as the description proceeds.

Objects:

(1) To provide various formulations, for use upon dental flosses, that are not only help whiten interproximal and subgingival dental surfaces but also taste good.

(2) To provide a new and improved method of making said formulations.

(3) To help reduce oral plaques and the dental problems they cause.

Advantages:

(1) The flavour enhanced whitening dental floss disclosed herein utilizes extremely small titanium dioxide particles which can be absorbed or otherwise retained by the enamel of the teeth. The result provides not only extended whiteness but a smooth finish that resists discoloration and attack.

(2) The delivery of the titanium dioxide particles to the interproximal surfaces and subgingival areas of the teeth is superior to any brush and dentifrice or mouthwash presently available.

(3) The enhanced flavour characteristics of a flavour enhanced whitening dental floss is superior to any other similar floss currently available.

(4) Fluoride based compounds may be used within the flavour enhanced whitening dental floss to significantly reduce the incidence of dental decay.

(5) In addition to pigmenting the enamel surfaces of teeth, titanium dioxide can be used as a mild abrading agent to help clean these same surfaces. Cleaner dental surfaces will, in turn, not only reduce dental decay but will also increase the effectiveness of most pigmenting agents, fluorides, and other medicaments.

(6) Professional dental personnel are not required. This not only reduces time but cost as well.

(7) The ingredients employed by the flavour enhanced whitening dental floss of this disclosure are cost competitive.

(8) The cost and mechanics of incorporating into the flavour enhanced whitening dental floss the various ingredients disclosed herein are both inexpensive and technically favourable.

SUMMARY OF THE INVENTION

The invention disclosed herein details a flavour enhanced whitening dental floss which can reduce dental plaques, and improve the interproximal and subgingival whiteness of teeth. Moreover, the enhanced flavour characteristics of this new floss are not only exceptional but long lasting as well.

To begin, dental plaques, which can contain 250 or more separate microbial species, use sugars and other fermentable carbohydrates to produce polymers which binds them to the tooth surface and acids which cause dental demineralization. In time, these plaques will produce caries and form calculus. The establishment of calculus can seriously irritate gum tissues and so promote the advance of periodontal disease. Do to its porous structure calculus can also harbour a multitude of bacterial plaques and so promote its continued spread. This makes effective oral hygiene impossible. Dental plaques are also capable of producing various offensive odours which, while not harmful, are self-evident in their undesirability.

In addition to the various problems created by plaques, consumers have always desired the cosmetic beauty of white shiny teeth. However, the stains and discolorment found in and around the interproximal surfaces of teeth are not only difficult to remove but are also difficult to prevent. Treatments for this condition are, however, only available from professional dental practitioners, certain dentifrices, some mouthwashes, and one floss. Unfortunately, professional dental practitioners are invariably expensive, time consuming, and not always effective, whereas, a brush and dentifrice alone are ineffective in cleaning, let alone actually whitening, the interproximal surfaces of teeth. Mouthwashes have been suggested by the prior art but as yet no commercial products have been realized that can efficiently clean or whiten these dental surfaces. A whitening floss has also been suggested by the prior art—specifically U.S. Pat. No. 6,102,050. However, this floss, while effective, releases only modest levels of flavouring.

A flavour enhanced whitening dental floss, however, addresses these problems by administering various highly effective pigmenting formulations to and around the interproximal surfaces and subgingival areas of teeth. The pigmenting agent titanium dioxide is particularly useful for this task as it can be absorbed or retained by the enamel layer when very small. This therefore, allows it to occupy the space between the hydroxyapatite crystals or prisms that make up this enamel layer. As a result, titanium dioxide particles, once deposited, are able to compete with substances that tend to attack, stain or discolor teeth by filling the space between the prisms with an inert white material instead of an undesirable substance or coloring.

In addition, floss formulations prepared using a Staged Preparation Technique offers consumers a product that not only tastes remarkably good but is also long lasting. In turn, this makes flossing a much more pleasurable experience than would otherwise be possible.

Fluorides can also be employed in order to reduce dental decay. Sweeteners can also be used as well as other ingredients or compounds. These may include, other pigmenting agents, polishing and abrading agents, and peroxide based compounds, alone or in combination.

As a result, a flavour enhanced whitening dental floss can offer many benefits. It can, for example, diminish dental plaques and other related dental diseases. Cosmetically, teeth will tend to be whiter and appear healthier. Taste has also been greatly improved over and above any other similarly produced product and, in final summation, all of this can be accomplished in a manner that is convenient, inexpensive, and safe.

BRIEF DESCRIPTION OF THE DRAWINGS

Not applicable.

DETAILED DESCRIPTION OF THE INVENTION

Introduction

The present invention pertains to a flavour enhanced whitening dental floss or FEWD floss that not only tastes good but which can also be used to help reduce the incidence of or the effects associated with dental plaques and the stains and discolorment found in and around the interproximal and subgingival surfaces of teeth. While these objectives are obviously desirable they are achieved in a most unique and novel manner by including, in this FEWD floss, various specialized ingredients. In addition, by utilizing a Staged Preparation Technique these ingredients can be blended into various formulations that are not only highly effective but good tasting as well.

As such, it is to this end that the following description is therefore provided to enable any person skilled in the art to make and use the invention herein disclosed. Various modifications, however, will remain readily apparent to those skilled in the art, as the generic principles of the present invention have been defined herein specifically to provide for the description of a FEWD floss.

That said, a FEWD floss of the present invention begins with a basic or root structure that comprises at least one suitable or commercially available dental floss, binder, emulsifying agent, pigmenting agent, solubilizing agent, flavouring agent, and sweetening agent. If desired, one or more fluoride compounds may also be used. While other ingredients may also be added to achieve various other effects, these primary compounds will form the basic or root formulations used herein. However, it must also be understood that all ingredients, compounds or components, regardless of the final formulation used, must be safe, present no danger to the body, teeth or soft tissues of the mouth nor create a discolorment in their appearance. Moreover, they should be inexpensive, easy to use and apply, non-irritating, and require minimal application time. Their individual procurement may also be derived from either natural or synthetic sources or a combination thereof so as to maximize formulation flexibility and manufacturing logistics.

With these thoughts in mind, the description will now individually detail these root components first, in order to more fully explain their individual compositions, applications, and functions. Thereafter, the description will detail various additional components, novel formulations and balancing methods thereof, Staged Preparation Techniques, and finally end with the addendum.

Dental Flosses

The meaning of the words, "dental floss(es)", shall be herein understood to include both dental flosses and dental tapes as well as any other similar article. Moreover, the dental flosses and tapes used in the present invention may include any suitable or commercially available dental floss or tape. These flosses and tapes can also be fabricated from either natural or synthetic sources examples of which include, but are not limited to, filaments or yarns of high and normal tenacity polymers, nylons, polyolefins, polyethylenes, polypropylenes, fluorocarbon compounds, polytetrafluoroethylenes, rayons, dacrons, acrylics, acetate polymers, and other plastics alone or in combination. Natural substances may include, but are not limited to, cotton, wool, silk, linen, and other staple fibres alone or in combination. Blends of synthetic-natural fibres can also be used. However, synthetic filaments are preferred for they are more durable, stronger, generally less expensive, and easier to work and procure.

The length, diameter, structure or design of the floss itself is also not limited to any specific size, shape, arrangement or configuration and thus, can be fabricated to suite any specific intention. It can, for example, be composed of a plurality of individual filaments that have been formed together to give a larger thread having a sufficiently small diameter to permit insertion between the teeth. It can also comprise a composite multifilament yarn bonded to an extruded monofilament or to another multifilament yarn. A single circular, square or rectangular shaped monofilament thread is also useful. Other suitable variations are also well known in the art and as such are also useable in the invention disclosed herein.

Binders

Binders are used in the invention disclosed herein to bind or otherwise attach to a dental floss the ingredients herein specified by this disclosure. They also provide the ability to alter the frictional characteristics of dental floss as well as help bind together the individual filaments comprising the floss itself. Moreover, the varieties used herein are not restricted to any specific types or compositions and are thus, given great freedom in their formulations, structures or make-ups. Examples of some suitable binders may therefore include, but are not limited to, natural waxes from insects, animals or plants, synthetic waxes, petroleum waxes such as polyethylene glycol wax, microcrystalline wax, liquid polyethylene glycol esters of beeswax as well as other water soluble or non-water soluble wax or wax-like compounds, or water soluble or non-water soluble polymers, soaps, gums, resins, and other substances known in the art.

Emulsifying Agents

All FEWD flosses must make use of one or more emulsifying agents which may include, but are not limited to, sorbitan monostearate, polysorbate 60, and the like, alone or in combination. Their use, within the formulations listed below, will allow individual chemical compounds to better interact, disperse, and disseminate during production as well as spread upon various dental surfaces in a much more efficient and effective manner. In turn, this makes the final product not only better but more consistent as well.

However, it must also be noted that while sorbitan monostearate and polysorbate 60 may both be used within a given formulation they must never be blended, mixed or combined simultaneously. That is because it makes certain ingredients clump together or react in various other undesirable ways.

Pigmenting Agents

All FEWD flosses must also make use of one or more dental pigmenting or coloring agents as their primary function is to whiten interproximal and subgingival dental surfaces and to maintain this whiteness for as long as possible. Suitable pigmenting agents may also be used to color the filaments or fibres comprising the floss as a means of producing a decorative effect or as a means of signifying or designating certain formulations.

Pigmenting agents such as these may therefore be obtained from either natural or synthetic sources, or a combination thereof. Thus, by way of example and not limitation, some common available coloring agents may therefore include FD and C-type dyes and lakes, fruit and vegetable extracts, titanium dioxide, and the like, alone or in combination. However, titanium dioxide is preferred for whitening teeth because of its brilliant opaque white color and its extremely small particle size.

Though a larger size may be used, titanium dioxide particles which have been found useful in the present invention have an approximate size of 1.5 microns or less, but preferably an approximate size of 0.1 microns or less, and most preferably an approximate size of 0.04 microns or less. That is because pigmenting agents such as these are able to be absorbed or retained by the enamel and dentinal layers of the teeth and so occupy the space between the hydroxyapatite crystals or prisms that make up these layers. In this way, these small titanium dioxide particles can compete with the substances that tend to attack, stain or discolor teeth by filling the space between the prisms with an inert white material instead of an undesirable substance or coloring.

A further benefit of titanium dioxide as the pigmenting agent is its ability to also function as a mild polishing or abrading agent when it is being used. Moreover, it can also be easily incorporated into the formulations listed below by utilizing a Staged Preparation Technique or by other similar or conventional means.

Solubilizing Agents

FEWD floss formulations will also make use of one or more solubilizing agents. Their function as such, will be to aid in dissociation. Suitable solubilizing agents may therefore include, but are not limited to, filtered water, reverse osmosis water, distilled water, and deionized water, alone or in combination. However, deionized water has been found preferable to the others.

Flavouring Agents

FEWD flosses may also utilize one or more flavouring agents. These may comprise essential oils, synthetic flavours, or mixtures thereof including, but not limited to, oils derived from plants and fruits such as citrus oils, fruit essences, mint, peppermint oil, spearmint oil, clove oil, oil of wintergreen, anise, sassafras, sage, eucalyptus, marjoram, cinnamon, lemon, orange, banana, cherry, apple, pineapple, grape, strawberry, blueberry, tutti frutti, methyl salicylate, Hagelin flavouring #640047, Hagelin flavouring #640057, Hagelin flavouring #671009, Hagelin flavouring #671010, and the like. Those skilled in the art will recognize that natural and artificial flavouring agents may be used independently or combined in any sensorially acceptable blend. All such flavours and flavour blends are contemplated by the present invention. However, it should also be noted that liquid based flavourings are preferred over powdered varieties as they tend to blend more easily with other ingredients and substances.

Sweetening Agents

To foster greater consumer appeal FEWD flosses may also contain one or more natural or artificial sweetening agents, alone or in combination. These may include, but are not limited to, sucrose, lactose, dextrose, maltose, dextrin, dried inverted sugar, fructose, levulose, galactose, corn syrup and their solids, sorbitol, mannitol, xylitol, hydrogenated starch hydrolysates, maltitol, sucralose, aspartame, salts of acesulfame, alitame, saccharin and its salts, cyclamic acid and its salts, glycyrrhizin, dihydrochalcones, thaumatin, monellin, and the like. Though any type or blend of sweetener may be used artificial compounds are preferred for they substantially reduce the potential for cariogenic decay.

Fluorides

Fluorides have in the past been found to help prevent the incidence of carious lesions or caries. Caries are caused when teeth demineralize at a rate faster than they remineralize and most demineralization is caused by acid producing dental plaques. Remineralization, however, is promoted by calcium and phosphate, the chief remineralizing agents found also in saliva. Fluoride based compounds, therefore, provide protection from carious lesions or caries by acting as a catalyst to speed the precipitation of calcium phosphate, in the form of a hydroxy apatite, onto or into teeth. However, this is not fluoride's only role. It is also able to inhibit the activity of some bacterial enzymes and their acid producing processes, and at extremely high concentrations it can also kill certain plaque bacteria. Even more important, it tends to become incorporated into the apatite, as a fluoridated hydroxy apatite or "fluorapatite", creating a mineral that is appreciably less dissolvable by acid.

Hence, FEWD flosses may contain one or more fluoride based compounds. These compounds may also be slightly soluble in water or may be fully water soluble. They are, however, foremost characterized by their ability to release fluoride ions in water and their freedom from undesired reactions with the FEWD floss's other compounds. Among these materials are numerous fluoride based compounds which can comprise inorganic fluoride salts such as soluble alkali metal, alkaline earth metal salts, and others. Examples of such include, but are not limited to, sodium fluoride, potassium fluoride, ammonium fluoride, a copper fluoride such as cuprous fluoride, zinc fluoride, sodium fluorosilicate, ammonium fluorosilicate, sodium fluorozirconate, barium fluoride, calcium fluoride, sodium monofluorophosphate, sodium silicofluoride, aluminum mono- and di-fluorophosphate, and fluorinated sodium calcium pyrophosphate. However, alkali metal fluorides, and mixtures thereof, are preferred with sodium fluoride being considered best.

When a fluoride compound is employed, the amount used is dependent to a large extent upon the type of fluorine compound, its solubility, and the final formulation and structure selected. As such, substantial leeway is given to the quantities or amounts used as long as normal formulation and pharmaceutical safeguards are observed.

Consequently, whenever fluoride based compounds are used within the formulations listed below they should amount to no more than 0.30 percent (W/W). However, it has been found that setting the maximum range at 0.24 percent (W/W) is preferable with 0.22 to 0.24 percent (W/W) being the best overall range to use.

Optimizing the effects and benefits of fluorides as well as other medicaments is also of prime importance to both manufactures and consumers alike. One way of accomplishing this is to provide as plaque free a dental enamel surface as possible. That is because most medicaments, in general, tend to function better when given a cleaner dental surface on which to work. In this respect, the incorporation into a FEWD floss of one or more peroxide based compounds, polishing or abrading agents, or other similar scrubbing or cleaning ingredients can improved results because such substances tend to attack and remove plaques. As these plaques diminish, the dental and oral impact of various medicaments will be much more effective and useful.

Polishing or Abrading Agents

One or more polishing or abrading agents may also be utilized in FEWD flosses. Moreover, the type of abrading agents employed are not restricted to any specific types or quantities. This, therefore, allows the abrading compounds used to better suit the final effects desired. In any case, their incorporation will help clean and polish teeth and so help produce a smooth and shiny surface that will resist discoloration, bacterial accumulation, and retention. Cleaner teeth also help to improve the therapeutic performance of other ingredients such a fluorides as well as reduce the overall effects of oral acids and related demineralizations.

Thus, with these thoughts in mind, FEWD flosses may make use of one or more polishing or abrading agents which may include, but is not limited to, a boride, carbide, carbonate, bicarbonate, nitride, oxide, dioxide, phosphate, silicate or sulphide of such elements as aluminum, calcium, iron, magnesium, potassium, silicon, sodium, tin, titanium, tungsten, zinc, and zirconium, alone or in combination.

While sodium bicarbonate may therefore be used as a mild, safe, and inexpensive abrading agent its usefulness does not end there. It can, for instance, also function as an anti-odorant, and so offer some odour absorbing capabilities. Being a water soluble alkaline compound it also has the ability to neutralize some quantities of oral acids. It also has the ability to act as a disinfectant by releasing, during its decomposition, modest quantities of elemental oxygen. Moreover, the amount of sodium bicarbonate used within an FEWD floss may be adjusted to suite any specific taste, texture or formulation required. In some recipes it may even be desirable to omit its use altogether or conversely, the manufacturer may employ copious quantities to amplify its effects.

Though sodium bicarbonate is a preferential compound there may be instances where it may be necessary or desirable to substitute one or more alternate compounds in its place. Such times may arise, for example, when certain compounds utilized within a given formulation chemically interact with sodium bicarbonate in an undesirable manner. Nonetheless, these alternate substances, though less preferable than sodium bicarbonate, should still be water soluble and possess traits similar to those found in sodium bicarbonate. Such a compound may, therefore, include potassium bicarbonate. The exact solubility and alkalinity of potassium bicarbonate will vary from that provided by sodium bicarbonate but this can be compensated by varying the respective amount used. It can also be used alone or in combination with sodium bicarbonate, and blended or otherwise incorporated into a FEWD floss in a fashion similar to that of sodium bicarbonate.

Peroxide Compounds

FEWD flosses may also make use of one or more peroxide based compounds such as, but not limited to, calcium peroxide, sodium carbomate peroxide, and sodium carbonate peroxide. Their use will help remove dental plaques and whiten teeth and so thereby reduce the incidence of dental caries and other related diseases. This ability to reduce dental decay stems from the fact that oxygen is released during their decompositions. Thus, when a peroxide based compound is utilized in the mouth the decomposal release of oxygen will not only vigorously attack bacterial plaques but also help whiten teeth. In addition, peroxide based compounds being mostly alkaline in nature will also help facilitate the neutralization of oral acid. Over time, as these plaques and acidic byproducts are reduced the progression of carious lesions and that of calculus accumulation upon the teeth is also substantially curtailed.

When, therefore, one or more peroxide based compounds are used, their individual concentrations will vary to some extent upon the types of peroxide compounds employed and the final formulation used in the FEWD floss. As a result, substantial leeway in both use and concentration is allowed but both the quantity as well as the level of alkalinity must be of a safe level. Assimilation of these peroxide compounds into the FEWD floss can be performed in a fashion similar to, but not limited to, that used by polishing or abrading agents.

FORMULATIONS

The information so far presented has given the reader the ability to produced a large number of floss formulations. With this in mind, the disclosure will now detail, using a percent weight per weight (W/W) format, four specific examples which can be used to produce the effects desired. Thus, by way of example and not limitation, the following formulations comprise:

Formulation Number One (a) one or more binders to a maximum of about 65.0 percent (WIW), with 45.22 percent (W/W) being optimal;

(b) one or more pigmenting agents to a maximum of about 25.8 percent (W/W), with 22.80 percent (W/W) being optimal;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal;

(f) one or more second emulsifying agents to a maximum of about 10.0 percent (W/W), with 3.0 percent (W/W) being optimal;

(g) one or more sweetening agents to a maximum of about 1.0 percent (W/W), with 0.2 percent (W/W) being optimal.

Formulation Number Two (a) one or more binders to a maximum of about 65.0 percent (W/W), with 45.00 percent (W/W) being optimal;

(b) one or more pigmenting agents to a maximum of about 25.8 percent (W/W), with 22.80 percent (W/W) being optimal;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal;

(f) one or more second emulsifying agents to a maximum of about 10.0 percent (W/W), with 3.0 percent (W/W) being optimal;

(g) one or more sweetening agents to a maximum of about 1.0 percent (W/W), with 0.2 percent (W/W) being optimal.

(h) one or more fluoride compounds to a maximum of about 0.30 percent (W/W), with about 0.22 percent (W/W) being optimal.

Formulation Number Three (a) one or more binders to a maximum of about 60.0 percent (W/W), with 48.22 percent (W/W) being optimal;

(b) one or more pigmenting agents to a maximum of about 30.0 percent (W/W), with 22.80 percent (W/W) being optimal;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal; and (f) one or more sweetening agents to a maximum of about 1.0 percent (W/W), with 0.2 percent (W/W) being optimal.

Formulation Number Four (a) one or more binders to a maximum of about 60.0 percent (W/W), with 48.00 percent (W/W) being optimal;

(b) one or more pigmenting agents to a maximum of about 30.0 percent (W/W), with 22.80 percent (W/W) being optimal;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal; and (f) one or more sweetening agents to a maximum of about 1.0 percent (W/W), with 0.2 percent (W/W) being optimal.

(g) one or more fluoride compounds to a maximum of about 0.30 percent (W/W), with about 0.22 percent (WIW) being optimal.

Formulations: Preferential Ingredients

The reader should also understand that while many different ingredients, compounds, and substances may be used in the above four formulations the following substances have been found to be preferable.

| | | |
|---|---|---|
| (1) | Binders: | preferably microcrystalline wax. |
| (2) | Pigmenting Agents: | preferably titanium dioxide. |
| (3) | Solubilizing Agents: | preferably deionized water. |
| (4) | First Emulsifying Agents: | preferably sorbitan monostearate. |
| (5) | Second Emulsifying Agents: | preferably polysorbate 60. |
| (6) | Sweetening Agents: | preferably sodium saccharin. |
| (7) | Fluoride Compounds: | preferably sodium fluoride. |

Flavourings, on the other hand, are basically unrestricted as both selection and concentration are generally governed by consumer preferences, logistical availability, or cost considerations. In other words, they have no real or actual bearing upon the safety or efficacy of the final product itself. However, four flavourings have been found to be distinctive, aromatic, long lasting, and desirable. They are Hagelin flavouring #640047, Hagelin flavouring #640057, Hagelin flavouring #671009, and Hagelin flavouring #671010, used alone or in combination. As such, these four flavourings, and others like them, shall be given preferential status within this invention so as to set it apart or distinguish it from competitors. Note also, that Hagelin flavourings may be procured from Hagelin & Company, Inc., 200 Meister Avenue, Branchburg, N.J., U.S.A., 08876-6033.

Quantitative Formulation Balancing

First and foremost, the reader must clearly understand that any variances or deviations from a formulation's stated optimal figures must be accounted for, on a similar percentage weight per weight basis, in one or more of the other components. What this means, in other words, is that a quantitative reduction or increase in the amount of flavouring used, or for that matter any other ingredient, must be accounted for by similarly or respectively increasing or decrease the quantity of one or more of the other components listed. This allows the sum of a formulation's component (W/W)s to still total 100 percent.

For example, if the flavouring used within formulation number one is reduced from 3.0 percent (W/W) to 1.0 percent (W/W) it will require a correspondingly similar increase in the amount of microcrystalline wax used. As such, the original optimal tally of microcrystalline wax must be increased from 45.22 percent (W/W) to 47.22 percent (W/W) of the formulation. This type of procedure shall, for the purpose of this disclosure, be herein referred to as Quantitative Formulation Balancing.

If a fluoride compound is also to be employed, within any of the above formulations, then the amount of microcrystalline wax used must also be quantitatively diminished by that same amount. Thus, for example, if 0.22 percent (W/W) sodium fluoride is to be utilized within formulation number one then the quantity of microcrystalline wax must be similarly or respectively reduced by that same amount and so total 45.22 minus 0.22 or 45.00 percent (W/W) of the formulation.

In most cases herein disclosed, Quantitative Formulation Balancing may be respectively achieved, on a (W/W) basis, by a similar inverse decrease or increase in the amount of microcrystalline wax employed. As such, it becomes self-evident that the purpose of microcrystalline wax is not just to provide lubrication, thread binding, and component scaffolding but formulation balancing as well.

Although microcrystalline wax may offer or yield a number of formulation balancing opportunities other ingredients may also be used. As such, two charts are conveniently provided below so that the reader may more fully understand various Quantitative Formulation Balancing techniques and the opportunities that they offer to individually tailor certain formulations to specific needs.

Quantitative Formulation Balancing (Formulations 1 and 2)

Take note: a formulation's optimal (W/W) figures are used as the base or reference line during any Quantitative Formulation Balancing. Consequently, any ingredients added or subtracted are referenced back to this starting point.

Secondly, the preferential substances specified below are for illustrative purposes only and thus shall not be used to limit the scope of the Quantitative Formulation Balancing technique herein disclosed.

Decreasing from Optimal:

(a) Microcrystalline wax:
Balance by first increasing deionized water first to suit. If necessary, increase sorbitan monostearate second, followed by flavouring last.

(b) Titanium dioxide particles:
Balance by first increasing microcrystalline wax. If needed, balance by adding deionized water next, followed by sorbitan monostearate last.

(c) Deionized water:
Balance to desired quantities by decreasing microcrystalline wax by a that same quantity and increasing sorbitan monostearate by twice that same quantity.

(d) Sorbitan monostearate:
Balance by first increasing microcrystalline as needed. Then, if necessary, continue balancing by adding deionized water second, followed by polysorbate 60 last.

(e) Flavouring:
Increase microcrystalline wax first. Then, if needed, add deionized water to complete any further balancing requirements.

(f) Polysorbate 60:
Balance by first adding sorbitan monostearate. Then, if further balancing is necessary, raise the amount of deionized water and/or microcrystalline wax next.

(g) Sodium saccharin:
Balance by first increasing flavouring to desired amount. Next, add deionized water for any further balancing needs.

(h) Sodium fluoride:
Balance by increasing microcrystalline wax by the same amount.

Increasing from Optimal:

(a) Microcrystalline wax:
Balance by first decreasing the amount of deionized water to suit. If any further balancing is required, reduce sorbitan monostearate second followed by flavouring, last.

(b) Titanium dioxide particles:
Balance by first decreasing deionized water as required. If further balancing is needed, lower the amount of microcrystalline wax next followed by sorbitan monostearate last.

(c) Deionized water:
Balance by reducing the flavouring the same amount.

(d) Sorbitan monostearate:
Balance by first decreasing the quantity of microcrystalline wax. Then, if necessary, continue balancing by reducing deionized water next. If further balancing is still required reduce polysorbate 60 last.

(e) Flavouring:
Balance by first decreasing the amount of deionized water to suit. If necessary, reduce microcrystalline wax to complete any further balancing needs.

(f) Polysorbate 60:
Balance by first decreasing microcrystalline wax, followed by titanium dioxide last.

(g) Sodium saccharin:
Balance by first reducing the amount of flavouring as needed. If further balancing is required, lower the amount of polysorbate 60 next.

(h) Sodium fluoride:
Balance by reducing microcrystalline wax by the same amount.

Quantitative Formulation Balancing (Formulations 3 and 4)

Take note: a formulation's optimal (W/W) figures are used as the base or reference line during any Quantitative Formulation Balancing. Consequently, any ingredients added or subtracted are referenced back to this starting point.

Secondly, the preferential substances specified below are for illustrative purposes only and thus shall not be used to limit the scope of the Quantitative Formulation Balancing technique herein disclosed.

Decreasing From Optimal:

(a) Microcrystalline wax:
Balance by first increasing sorbitan monostearate as needed. Then, if necessary, complete any further balancing requirements by adding deionized water and/or flavouring next.

(b) Titanium dioxide particles:
Balance by first increasing the amount of microcrystalline wax to suit. Next, increase the amount of deionized water, followed by sorbitan monostearate last.

(c) Deionized water:
Balance by increasing the amount of microcrystalline wax first. Then, if necessary, add titanium dioxide next, followed by sorbitan monostearate last.

(d) Sorbitan monostearate:
Balance by first increasing the amount of microcrystalline wax as needed. If further balancing is required, raise the amount of titanium dioxide next, followed by deionized water last.

(e) Flavouring:
Balance by raising the quantity of microcrystalline wax first, followed by titanium dioxide second, and sorbitan monostearate last.

(g) Sodium saccharin:
Balance by increasing the amount of microcrystalline wax and/or flavouring first. If required, increase the amount of titanium dioxide second, followed by sorbitan monostearate last.

(h) Sodium fluoride:
Balance by increasing microcrystalline wax by the same amount.

Increasing from Optimal:

(a) Microcrystalline wax:
Balance by first decreasing the quantity of deionized water. Then, if necessary, complete any balancing needs by reducing the amount of sorbitan monostearate as required.

(b) Titanium dioxide particles:
Balance by first increasing the amount of microcrystalline wax by the same amount in order to compensate for the lack of polysorbate 60. Next, reduce the amount of deionized water. Then, if further balancing is required, decrease the quantity of sorbitan monostearate to suit.

(c) Deionized water:
Balance by first reducing microcrystalline wax as needed. Next, lower the amount of titanium dioxide second, followed by sorbitan monostearate last.

(d) Sorbitan monostearate:
Balance by reducing microcrystalline wax as required.

(e) Flavouring:
Balance by decreasing the amount of deionized water to suit first, followed by sodium saccharin last.

(g) Sodium saccharin:
Balance by reducing the amount of flavouring as required.

(h) Sodium fluoride:
Balance by reducing microcrystalline wax by the same amount.

Note also, that in order to help preserve chemical efficacy over extended periods and prevent chemical interactions during storage sweetening agents, fluoride compounds, flavourings and other compounds may be encapsulated or microcoated. In addition, the encapsulating or microcoating materials used within each formulation should be the same in order to provide a simultaneous release and interaction of the chemical compounds used. Examples of some suitable encapsulating or microcoating substances may include, but are not limited to, ethylcellulose, methyl cellulose, sodium carboxymethyl cellulose, and other coating polymers or materials which can coat and preserve the ingredients until released by the mechanical action of flossing and or the usual enzymatic action provided by saliva.

Moreover, within a given formulation, each ingredient is permitted a range or a tolerance of about plus or minus five percent of the amount specified in order to allow for manufacturing variances. Thus, for example, sodium saccharin which has been herein specified as 0.20 percent (W/W) in all of the above formulations may actually range from 0.19 to 0.21 percent (W/W).

Finally, the four formulations detailed above may be prepared and deposited upon various dental flosses by using conventional equipment, machinery, and production facilities in conjunction with the following method:

Staged Preparation Technique (a) This method begins by first melting one or more binders, preferably microcrystalline wax, within a suitable container until they are liquified.

(b) Once these binders have been liquified, one or more first emulsifying agents, preferably sorbitan monostearate, are then added in a conventional manner to the liquified binders produced in step (a). The resulting composition is then mixed until visually homogenous.

(c) One or more second emulsifying agents, preferably polysorbate 60, are now added in a conventional manner to the liquified composition produced by step (b). The resulting composition is then, once again, mixed until visually homogenous. In formulations devoid of a second emulsifying agents, such as in formulations 3 and 4 detailed above, this step is to be bypassed or otherwise deleted.

(d) A second container is now procured and in it is thoroughly mixed, using conventional methods and until visually homogenous, all other ingredients. These ingredients will include, but are not limited to, one or more solubilizing agents, preferably deionized water; flavouring agents; and sweetening agents, preferably sodium saccharin. If any fluoride based compounds or other ingredients are also to be used they are added, along with the others, at this time.

(e) Once the composition of step (d) has been prepared it is then added to the mixture produced by step (c) and thoroughly mixed, using conventional means, until visually homogenous.

(f) One or more pigmenting agents, preferably titanium dioxide, are now added to the resultant composition produced in step (e). This new composition is then mixed, in a convention manner, until visually homogenous.

(g) The resulting composition produced by step (f) is then uniformly applied to dental floss using conventional techniques.

For purposes of this disclosure the above seven step method of producing a FEWD floss shall be herein called a Staged preparation Technique. Using this method will assure the production of a high quality good tasting whitening floss time and time again. It must also be understood, that although this method is highly preferred other techniques are possible. As a result, the method provided herein should be considered illustrative and not limitative in nature.

Addendum

The following patents and other references, the entire contents of which are hereby incorporated by reference into this specification, offer the reader a supplementary appendage of current pharmacological and therapeutical information, flossing ingredients, components, and manufacturing methods. As such, this information may therefore be use, as required, in the production of all FEWD flosses herein described.

| | | |
|---|---|---|
| (1) | U.S. Pat. No. : | 5,573,850 |
| | Invented by: | David V. Cunningham, Sheldon Kavesh, and Christopher P. Griffin. |
| | Issued: | Nov. 12, 1996 |
| (2) | U.S. Pat. No. : | 5,560,377 |
| | Invented by: | Marion Donovan. |
| | Issued: | Oct. 1, 1996 |
| (3) | U.S. Pat. No. : | 5,526,831 |
| | Invented by: | Sean G. Gilligan, Dermot T. Freeman, Larry J. Oliphant, Jeffrey S. Meessmann, Patrick J. Hanley, and Gerald S. Szczech. |
| | Issued: | Jun. 18, 1996 |
| (4) | U.S. Pat. No. : | 5,423,337 |
| | Invented by: | Gary Ahlert. |
| | Issued: | Jun. 13, 1995 |
| (5) | U.S. Pat. No. : | 5.357,990 |
| | Invented by: | Christopher H. Suhonen, and John A. Kaminski. |
| | Issued: | Oct. 25, 1994 |
| (6) | U.S. Pat. No. : | 5,353,820 |
| | Invented by: | Christopher H. Suhonen, and Pedro L. Jusino. |
| | Issued: | Oct. 11, 1994 |
| (7) | U.S. Pat. No. : | 5,220,932 |
| | Invented by: | Jacob M. Blass. |
| | Issued: | Jun. 22, 1993 |
| (8) | U.S. Pat. No. : | 5,209,251 |
| | Invented by: | John P. Curtis, and James H. Kemp. |
| | Issued: | May 11, 1993 |

-continued

| | | |
|---|---|---|
| (9) | U.S. Pat. No. : | 5,098,711 |
| | Invented by: | Ira Hill, and Robert D. White. |
| | Issued: | Mar. 24, 1992 |
| (10) | U.S. Pat. No. : | 4,548,219 |
| | Invented by: | Michael G. Newman. |
| | Issued: | Oct. 22, 1985 |
| (11) | Accepted Dental Therapeutics, 39th Edition, Copyright 1982, by the American Dental Association, 211 E. Chicago Ave., Chicago, Illinois, U.S., 60611. Library of Congress Number: 74[2]-MCAT | |
| (12) | Comprehensive Dental Hygiene Care, 4th Edition, Written by: Irene R. Woodall, Copyright 1993, by Mosby-Year Book, Inc., 11830 Westline Industrial Drive, St. Louis, Missouri, U.S., 63146. ISBN: 0-8016-7019-5 | |
| (13) | The Merck Manual, Executive Editor: Keryn A. G. Lane, Copyright 1999, by Merck and Co., Inc., Whitehouse Station, N.J., U.S., Publisher: Gary Zelko. ISBN: 0911910-10-7 | |
| (14) | Dental Clinics of North America, Pharmacology and Therapeutics, Publisher: W. B. Saunders, 1 Goldthorn Avenue, Canada, N8Z 5T9, ISSN: 0011-8532 | |
| (15) | Fenaroli's Handbook of Flavour Ingredients, Written by: Prof. Dr. Giovanni Fenaroli, Copyright 1971, by the Chemical Rubber Company, 18901 Cranwood Pkwy., Cleveland, Ohio, U.S., 44128. Library of Congress Number: 72-152143 | |
| (16) | Flavor Technology, Profiles, Products, Applications, Written by: Henry B. Heath, M.B.E., B. Pharm. (London), Copyright 1978, Avi Publishing Company Incorporated, Westport, Connecticut, U.S.. ISBN: 0-87005-258-9 | |

Additional information regarding the subject of this invention can be found in the many books available to the public at libraries and technical centres or in the many patents and government publications currently available today.

In conclusion, the reader must also understand that the preceding description contains many specificities that should not be construed as limiting the scope of the invention but as merely providing illustrations of some of the presently preferred embodiments thereof. As a result, the scope of the invention should thus be determined by the appended claims and their legal equivalents rather than by the examples given.

The embodiments of the invention in which an exclusive property or privilege is claimed are defined as follows:

1. A flavour enhanced whitening dental floss comprising a dental floss and a formulation, and wherein said formulation is selected from the group consisting of:

Formulation Number One, wherein Formulation Number One comprises:

(a) one or more binders to a maximum of about 65.0 percent (W/W), with 45.22 percent (W/W) being optimal;

(b) one or more pigmenting agents to a maximum of about 25.8 percent (W/W), with 22.80 percent (W/W) being optimal, and wherein some or all of said pigmenting agents are comprised of inert white particulate, and wherein said inert white particulate is sufficiently small to be depositable by said flavour enhanced whitening dental floss onto or into the enamel and dentinal layers of the teeth in order to occupy those spaces between the hydroxyapatite crystals or prisms found therein;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal;

(f) one or more second emulsifying agents to a maximum of about 10.0 percent (W/W), with 3.0 percent (W/W) being optimal; and (g) one or more sweetening agents to a maximum of about 1.0 percent (W/W), with 0.2 percent (W/W) being optimal;

Formulation Number Two, wherein Formulation Number Two comprises:

(a) one or more binders to a maximum of about 65.0 percent (W/W), with 45.00 percent (W/W) being optimal;

(b) one or more pigmenting agents to a maximum of about 25.8 percent (W/W), with 22.80 percent (W/W) being optimal, and wherein some or all of said pigmenting agents are comprised of inert white particulate, and wherein said inert white particulate is sufficiently small to be depositable by said flavour enhanced whitening dental floss onto or into the enamel and dentinal layers of the teeth in order to occupy those spaces between the hydroxyapatite crystals or prisms found therein;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal;

(f) one or more second emulsifying agents to a maximum of about 10.0 percent (W/W), with 3.0 percent (W/W) being optimal;

(g) one or more sweetening agents to a maximum of about 1.0 percent (W/W), with 0.2 percent (W/W) being optimal; and (h) one or more fluoride compounds to a maximum of about 0.30 percent (W/W), with about 0.22 percent (W/W) being optimal;

Formulation Number Three, wherein Formulation Number Three comprises:

(a) one or more binders to a maximum of about 60.0 percent (W/W), with 48.22 percent (W/W) being optimal;

(b) one or more pigmenting agents to a maximum of about 30.0 percent (W/W), with 22.80 percent (W/W) being optimal, and wherein some or all of said pigmenting agents are comprised of inert white particulate, and wherein said inert white particulate is sufficiently small to be depositable by said flavour enhanced whitening dental floss onto or into the enamel and dentinal layers of the teeth in order to occupy those spaces between the hydroxyapatite crystals or prisms found therein;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal; and (f) one or more sweetening agents to a maximum of about 1.0 percent (W/W), with 0.2 percent (W/W) being optimal;

Formulation Number Four, wherein Formulation Number Four comprises:

(a) one or more binders to a maximum of about 60.0 percent (W/W), with 48.00 percent (W/W) being optimal;

(b) one or more pigmenting agents to a maximum of about 30.0 percent (W/W), with 22.80 percent (W/W) being optimal, and wherein some or all of said pigmenting agents are comprised of inert white particulate, and wherein said inert white particulate is sufficiently small to be depositable by said flavour enhanced whitening dental floss onto or into the enamel and dentinal layers of the teeth in order to occupy those spaces between the hydroxyapatite crystals or prisms found therein;

(c) one or more solubilizing agents to a maximum of about 30.0 percent (W/W), with 18.78 percent (W/W) being optimal;

(d) one or more first emulsifying agents to a maximum of about 10.0 percent (W/W), with 7.0 percent (W/W) being optimal;

(e) one or more flavouring agents to a maximum of about 25.0 percent (W/W), with 3.0 percent (W/W) being optimal; and (f) one or more sweetening agents to a maximum of about 1.0 percent (W/W), with 0.2 percent (W/W) being optimal;

(g) one or more fluoride compounds to a maximum of about 0.30 percent (W/W), with about 0.22 percent (W/W) being optimal.

2. The claim as recited in claim 1 wherein said flavour enhanced whitening dental floss is made by using a Staged Preparation Technique.

3. The claim as recited in claim 2 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

4. The claim as recited in claim 3 wherein said inert white particulate is partially or entirely titanium dioxide.

5. The claim as recited in claim 2 wherein a Quantitative Formulation Balancing technique is used to adjust the formulations of the flavour enhanced whitening dental floss.

6. The claim as recited in claim 5 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

7. The claim as recited in claim 6 wherein said inert white particulate is partially or entirely titanium dioxide.

8. The claim as recited in claim 1 wherein a Quantitative Formulation Balancing technique is used to adjust the formulations of the flavour enhanced whitening dental floss.

9. The claim as recited in claim 8 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

10. The claim as recited in claim 9 wherein said inert white particulate is partially or entirely titanium dioxide.

11. The claim as recited in claim 1 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

12. The claim as recited in claim 1 wherein said inert white particulate is partially or entirely titanium dioxide.

13. A flavour enhanced whitening dental floss comprising a dental floss and a formulation, and wherein a Staged Preparation Technique is used to make said formulation; and wherein said formulation is selected from the group consisting of:

Formulation Number One, wherein Formulation Number One comprises:
(a) one or more binders to a maximum of about 65.0 percent (W/W), with 45.22 percent (W/W) being optimal;
(b) one or more pigmenting agents to a maximum of about 25.8 percent (W/W), with 22.80 percent (W/W) being optimal;
(c) one or more solubilizing agents to a maximum of about 30.0 percent (W/W), with 18.78 percent (W/W) being optimal;
(d) one or more first emulsifying agents to a maximum of about 10.0 percent (W/W), with 7.0 percent (W/W) being optimal;
(e) one or more flavouring agents to a maximum of about 25.0 percent (W/W), with 3.0 percent (W/W) being optimal;
(f) one or more second emulsifying agents to a maximum of about 10.0 percent (W/W), with 3.0 percent (W/W) being optimal; and
(g) one or more sweetening agents to a maximum of about 1.0 percent (W/W), with 0.2 percent (W/W) being optimal;

Formulation Number Two, wherein Formulation Number Two comprises:
(a) one or more binders to a maximum of about 65.0 percent (W/W), with 45.00 percent (W/W) being optimal;
(b) one or more pigmenting agents to a maximum of about 25.8 percent (W/W), with 22.80 percent (W/W) being optimal;
(c) one or more solubilizing agents to a maximum of about 30.0 percent (W/W), with 18.78 percent (W/W) being optimal;
(d) one or more first emulsifying agents to a maximum of about 10.0 percent (W/W), with 7.0 percent (W/W) being optimal;
(e) one or more flavouring agents to a maximum of about 25.0 percent (W/W), with 3.0 percent (W/W) being optimal;
(f) one or more second emulsifying agents to a maximum of about 10.0 percent (W/W), with 3.0 percent (W/W) being optimal;
(g) one or more sweetening agents to a maximum of about 1.0 percent (W/W), with 0.2 percent (W/W) being optimal; and
(h) one or more fluoride compounds to a maximum of about 0.30 percent (W/W), with about 0.22 percent (W/W) being optimal;

Formulation Number Three, wherein Formulation Number Three comprises:
(a) one or more binders to a maximum of about 60.0 percent (W/W), with 48.22 percent (W/W) being optimal;
(b) one or more pigmenting agents to a maximum of about 30.0 percent (W/W), with 22.80 percent (W/W) being optimal;
(c) one or more solubilizing agents to a maximum of about 30.0 percent (W/W), with 18.78 percent (W/W) being optimal;
(d) one or more first emulsifying agents to a maximum of about 10.0 percent (W/W), with 7.0 percent (W/W) being optimal;
(e) one or more flavouring agents to a maximum of about 25.0 percent (W/W), with 3.0 percent (W/W) being optimal; and
(f) one or more sweetening agents to a maximum of about 1.0 percent (W/W), with 0.2 percent (W/W) being optimal;

Formulation Number Four, wherein Formulation Number Four comprises:
(a) one or more binders to a maximum of about 60.0 percent (W/W), with 48.00 percent (W/W) being optimal;
(b) one or more pigmenting agents to a maximum of about 30.0 percent (W/W), with 22.80 percent (W/W) being optimal;
(c) one or more solubilizing agents to a maximum of about 30.0 percent (W/W), with 18.78 percent (W/W) being optimal;
(d) one or more first emulsifying agents to a maximum of about 10.0 percent (W/W), with 7.0 percent (W/W) being optimal;
(e) one or more flavouring agents to a maximum of about 25.0 percent (W/W), with 3.0 percent (W/W) being optimal;
(f) one or more sweetening agents to a maximum of about 1.0 percent (W/W), with 0.2 percent (W/W) being optimal; and
(g) one or more fluoride compounds to a maximum of about 0.30 percent (W/W), with about 0.22 percent (W/W) being optimal.

14. The claim as recited in claim 13 wherein a Quantitative Formulation Balancing technique is used to adjust the formulations of the flavour enhanced whitening dental floss.

15. The claim as recited in claim 14 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

16. The claim as recited in claim 15 wherein said pigmenting agents are comprised of inert white particulate.

17. The claim as recited in claim 13 wherein said binder is microcrystalline wax, said solubilizing agent is deionized water, said first emulsifying agent is sorbitan monostearate, said second emulsifying agent is polysorbate 60, said sweetening agent is sodium saccharin, and said fluoride compound is sodium fluoride.

18. The claim as recited in claim 17 wherein said pigmenting agents are comprised of inert white particulate.

19. The claim as recited in claim 13 wherein said pigmenting agents are comprised of inert white particulate.

20. A method for reducing dental plaques and caries, and whitening teeth, in and around the interproximal and subgingival areas, comprising the steps of:

(I) providing a dental floss;
(II) providing a formulation wherein said formulation is made using a Staged Preparation Technique, and wherein a Quantitative Formulation Balancing technique is used to adjust said formulation, and wherein said formulation is selected from the group consisting of:

Formulation Number One, wherein Formulation Number One comprises:
- (a) one or more binders to a maximum of about 65.0 percent (W/W), with 45.22 percent (W/W) being optimal;
- (b) one or more pigmenting agents to a maximum of about 25.8 percent (W/W), with 22.80 percent (W/W) being optimal;
- (c) one or more solubilizing agents to a maximum of about 30.0 percent (W/W), with 18.78 percent (W/W) being optimal;
- (d) one or more first emulsifying agents to a maximum of about 10.0 percent (W/W), with 7.0 percent (W/W) being optimal;
- (e) one or more flavouring agents to a maximum of about 25.0 percent (W/W), with 3.0 percent (W/W) being optimal;
- (f) one or more second emulsifying agents to a maximum of about 10.0 percent (W/W), with 3.0 percent (W/W) being optimal; and
- (g) one or more sweetening agents to a maximum of about 1.0 percent (W/W), with 0.2 percent (W/W) being optimal;

Formulation Number Two, wherein Formulation Number Two comprises:
- (a) one or more binders to a maximum of about 65.0 percent (W/W), with 45.00 percent (W/W) being optimal;
- (b) one or more pigmenting agents to a maximum of about 25.8 percent (W/W), with 22.80 percent (W/W) being optimal;
- (c) one or more solubilizing agents to a maximum of about 30.0 percent (W/W), with 18.78 percent (W/W) being optimal;
- (d) one or more first emulsifying agents to a maximum of about 10.0 percent (W/W), with 7.0 percent (W/W) being optimal;
- (e) one or more flavouring agents to a maximum of about 25.0 percent (W/W), with 3.0 percent (W/W) being optimal;
- (f) one or more second emulsifying agents to a maximum of about 10.0 percent (W/W), with 3.0 percent (W/W) being optimal;
- (g) one or more sweetening agents to a maximum of about 1.0 percent (W/W), with 0.2 percent (W/W) being optimal; and
- (h) one or more fluoride compounds to a maximum of about 0.30 percent (W/W), with about 0.22 percent (W/W) being optimal;

Formulation Number Three, wherein Formulation Number Three comprises:
- (a) one or more binders to a maximum of about 60.0 percent (W/W), with 48.22 percent (W/W) being optimal;
- (b) one or more pigmenting agents to a maximum of about 30.0 percent (W/W), with 22.80 percent (W/W) being optimal;
- (c) one or more solubilizing agents to a maximum of about 30.0 percent (W/W), with 18.78 percent (W/W) being optimal;
- (d) one or more first emulsifying agents to a maximum of about 10.0 percent (W/W), with 7.0 percent (W/W) being optimal;
- (e) one or more flavouring agents to a maximum of about 25.0 percent (W/W), with 3.0 percent (W/W) being optimal; and
- (f) one or more sweetening agents to a maximum of about 1.0 percent (W/W), with 0.2 percent (W/W) being optimal;

Formulation Number Four, wherein Formulation Number Four comprises:
- (a) one or more binders to a maximum of about 60.0 percent (W/W), with 48.00 percent (W/W) being optimal;
- (b) one or more pigmenting agents to a maximum of about 30.0 percent (W/W), with 22.80 percent (W/W) being optimal;
- (c) one or more solubilizing agents to a maximum of about 30.0 percent (W/W), with 18.78 percent (W/W) being optimal;
- (d) one or more first emulsifying agents to a maximum of about 10.0 percent (W/W), with 7.0 percent (W/W) being optimal;
- (e) one or more flavouring agents to a maximum of about 25.0 percent (W/W), with 3.0 percent (W/W) being optimal;
- (f) one or more sweetening agents to a maximum of about 1.0 percent (W/W), with 0.2 percent (W/W) being optimal; and
- (g) one or more fluoride compounds to a maximum of about 0.30 percent (W/W), with about 0.22 percent (W/W) being optimal;

(III) contacting said formulation with said dental floss by incorporating said formulation therein or as a topical applicant in order to thereby produce a flavour enhanced whitening dental floss; and (IV) flossing with said flavour enhanced whitening dental floss to thereby reduce said plaques and caries, and whiten said teeth.

21. A method for the production of dental floss formulations using a Staged Preparation Technique wherein said Staged Preparation Technique comprises the following steps:
- (a) This method begins by first melting one or more binders, preferably microcrystalline wax, within a suitable container until they are liquified;
- (b) Once these binders have been liquified, one or more first emulsifying agents, preferably sorbitan monostearate, are then added in a conventional manner to the liquified binders produced in step (a); The resulting composition is then mixed until visually homogenous;
- (c) One or more second emulsifying agents, preferably polysorbate 60, are now added in a conventional manner to the liquified composition produced by step (b); The resulting composition is then, once again, mixed until visually homogenous; In formulations devoid of a second emulsifying agents, such as in formulations 3 and 4 detailed above, this step is to be bypassed or otherwise deleted;
- (d) A second container is now procured and in it is thoroughly mixed, using conventional methods and until visually homogenous, all other ingredients; These ingredients will include, but are not limited to, one or more solubilizing agents, preferably deionized water; flavouring agents; and sweetening agents, preferably sodium saccharin; If any fluoride based compounds or other ingredients are also to be used they are added, along with the others, at this time;
- (e) Once the composition of step (d) has been prepared it is then added to the mixture produced by step (c) and thoroughly mixed, using conventional means, until visually homogenous;

(f) One or more pigmenting agents, preferably titanium dioxide, are now added to the resultant composition produced in step (e); This new composition is then mixed, in a convention manner, until visually homogenous;

(g) The resulting composition produced by step (f) is then uniformly applied to dental floss using conventional techniques.

* * * * *

UNITED STATES PATENT AND TRADEMARK OFFICE
CERTIFICATE OF CORRECTION

PATENT NO.     : 6,619,299 B2
DATED          : September 16, 2003
INVENTOR(S)    : Robert Victor Marcon and Lawrence Wayne Nash It is certified that error appears in the above-identified patent and that said Letters Patent is hereby corrected as shown below:

Column 2,
Line 36, delete "that are not only help" and substitute -- that not only help -- therefor.

Column 9,
Line 33, delete "65.0 percent (WIW)" and substitute -- 65.0 percent (W/W) -- therefor.
Line 49, delete "being optimal;" and substitute -- being optimal; and -- therefor.

Column 10,
Line 9, delete "being optimal." and substitute -- being optimal; and -- therefor.
Line 53, delete "being optimal; and" and substitute -- being optimal; -- therefor.
Line 56, delete "being optimal." and substitute -- being optimal; and -- therefor.
Line 60, delete "0.22 percent (WIW)" and substitute -- 0.22 percent (W/W) -- therefor.

Column 12,
Line 28, delete "wax by a that same" and substitute -- wax by that same -- therefor.
Line 31, delete "microcrystalline as needed" and substitute -- microcrystalline wax as needed -- therefor.

Column 14,
Line 63, delete "a second emulsifying agents" and substitute -- a second emulsifying agent -- therefor.

Column 18,
Line 26, delete "being optimal; and" and substitute -- being optimal; -- therefor.
Line 29, delete "being optimal;" and substitute -- being optimal; and -- therefor.

Column 22,
Line 50, delete "a second emulsifying agents" and substitute -- a second emulsifying agent -- therefor.

UNITED STATES PATENT AND TRADEMARK OFFICE
CERTIFICATE OF CORRECTION

PATENT NO. : 6,619,299 B2
DATED : September 16, 2003
INVENTOR(S) : Robert Victor Marcon and Lawrence Wayne Nash It is certified that error appears in the above-identified patent and that said Letters Patent is hereby corrected as shown below:

<u>Column 23,</u>
Line 5, delete "until visually homogenous;" and substitute -- until visually homogenous; and -- therefor.

Signed and Sealed this

Thirteenth Day of July, 2004

JON W. DUDAS
*Acting Director of the United States Patent and Trademark Office*